United States Patent
Kagan et al.

US006818239B2

(10) Patent No.: US 6,818,239 B2
(45) Date of Patent: Nov. 16, 2004

(54) PROCESSES FOR EXTRACTING CAROTENOIDS AND FOR PREPARING FEED MATERIALS

(75) Inventors: Michael Kagan, Jerusalem (IL); Sergei Braun, Zur Hadassa (IL)

(73) Assignee: Fermentron Ltd., Jerusalem (IL)

( * ) Notice: Subject to any disclaimer, the term of this patent is extended or adjusted under 35 U.S.C. 154(b) by 148 days.

(21) Appl. No.: 10/172,747

(22) Filed: Jun. 17, 2002

(65) Prior Publication Data

US 2003/0044495 A1 Mar. 6, 2003

Related U.S. Application Data

(63) Continuation of application No. PCT/IL00/00846, filed on Dec. 18, 2000.

(30) Foreign Application Priority Data

Dec. 21, 1999 (GB) .............................. 9930194

(51) Int. Cl.$^7$ .............................. A23L 1/28; A23L 1/27
(52) U.S. Cl. ....................... 426/429; 426/431; 426/478; 426/250; 426/253; 426/540
(58) Field of Search ................................ 426/807, 250, 426/253, 635, 425, 429, 430, 431, 478, 540; 424/439, 451

(56) References Cited

U.S. PATENT DOCUMENTS

| | | | | |
|---|---|---|---|---|
| 3,906,112 A | * | 9/1975 | Anderson .................... 426/1 |
| 4,225,734 A | | 9/1980 | McMurry .................... 585/351 |
| 4,439,629 A | | 3/1984 | Ruegg ........................ 585/803 |
| 4,505,936 A | * | 3/1985 | Meyers et al. ............... 426/1 |
| 4,851,339 A | * | 7/1989 | Hills ........................... 435/67 |
| 4,871,551 A | * | 10/1989 | Spencer ....................... 426/2 |
| 5,310,554 A | * | 5/1994 | Haigh ......................... 424/439 |
| 5,714,658 A | | 2/1998 | Heidlas et al. ............... 585/351 |
| 5,741,658 A | * | 4/1998 | Morrissey .................... 435/23 |
| 5,830,738 A | * | 11/1998 | Thomas et al. .............. 209/209 |
| 5,837,311 A | * | 11/1998 | Zelkha et al. ............... 426/651 |
| 5,897,866 A | * | 4/1999 | Bombardelli et al. ....... 424/777 |
| 6,055,936 A | * | 5/2000 | Collin ......................... 119/215 |
| 6,329,557 B1 | * | 12/2001 | Rodriguez et al. .......... 568/834 |
| 6,380,442 B1 | * | 4/2002 | Madhavi et al. ............ 568/816 |
| 6,399,105 B1 | * | 6/2002 | Collin ......................... 424/550 |
| 6,407,306 B1 | * | 6/2002 | Peter et al. .................. 585/833 |
| 2002/0082459 A1 | * | 6/2002 | Bailey et al. ............... 585/351 |
| 2003/0044499 A1 | * | 3/2003 | Zelkha et al. ............... 426/431 |
| 2003/0054070 A1 | * | 3/2003 | Bridges et al. .............. 426/73 |
| 2003/0087335 A1 | * | 5/2003 | Han et al. .................... 435/67 |
| 2003/0185939 A1 | * | 10/2003 | Neilsen ....................... 426/61 |

FOREIGN PATENT DOCUMENTS

| | | |
|---|---|---|
| EP | 0612725 A1 | 8/1994 |
| EP | 0670306 A1 | 9/1995 |
| EP | 0732378 A2 | 9/1996 |
| WO | WO96/29306 | 9/1996 |
| WO | WO98/03480 | 1/1998 |
| WO | WO98/50574 | 11/1998 |

* cited by examiner

*Primary Examiner*—N. Bhat

(57) ABSTRACT

A general process for the extraction of carotenoids from a carotenoid source such as a biomass, which may be various biomasses including the yeast *Phaffia rhodozyma*, comprises treating the carotenoid source at an elevated temperature with a solvent mixture comprising water, a hydrophobic carotenoid solvent such as vegetable oil and a water soluble co-solvent such as ethanol so as to extract the carotenoid source into the hydrophobic solvent. Benefits include (a) the ease of incorporation into the diet, (b) the increased bioavailability achieved and, (c) the ease of stabilization against oxidation.

16 Claims, No Drawings

PROCESSES FOR EXTRACTING CAROTENOIDS AND FOR PREPARING FEED MATERIALS

CROSS-REFERENCE TO RELATED APPLICATION

This is a continuation of PCT/IL00/00846, filed on 18 Dec. 2000, which claims convention priority from United Kingdom Patent Application No. 9930194.7 filed 21 Dec. 1999. PCT/IL00/00846 published under No. WO 01/46133 on 28 Jun. 2001; the publication is in English. A Demand for Chapter II was filed in PCTIL00/00846.

This invention relates to an extraction process for extracting carotenoids from carotenoid sources such as biomasses, which may be naturally-occurring or may be cultivated for the purpose. Such carotenoids find commercial application as pigments, anti-oxidants and food supplements, both for human and animal consumption.

Salmonids reared in the wild acquire a pink coloration resulting from the ingestion of micro-crustacea containing the red pigment astaxanthin as a natural part of their regular diet. When salmonids are reared in captivity, this is astaxanthin is artificially added to the feed in order to produce the desired pink coloration of the salmonid flesh. The amount of astaxanthin required to achieve this coloration is typically about 60 mg per kilogram of fish feed. Such pigments are also used to increase the skin colour of farmed fish such as sea bream and in shrimp farming.

Both synthetic and natural sources of astaxanthin have been used for salmonid pigmentation. The main source currently used is synthetic due to the high cost of natural-source formulations. Natural-source formulations, have included the direct incorporation of astaxanthin-rich biomass such as the yeast *Pfaffia rhodozyma*, the alga *Haematococcus pluvalis*, and crustacean products directly in the salmonid feed. However, said direct incorporation has not proved cost effective vis-à-vis the synthetic product due to the inability of the fish's digestive system to effectively extract the astaxanthin from the biomass cells; i.e. the low bioavailability of this source.

Other commercially important carotenoids including lycopene and β-carotene are also currently more expensive when extracted from natural sources than their synthetic counterparts.

Given the economic importance of astaxanthin and other carotenoids, numerous methods of optimizing the production of carotenoid-rich biomasses and improving carotenoid-extraction therefrom have been attempted.

The known natural sources of astaxanthin include shellfish, krill, the yeast *P. rhodozyma*, the green algae *Haematococcus pluvialis* and certain bacterial strains. Natural sources of lycopene include tomatoes and tomato waste, and carrots are a natural source of β-carotene.

Due to the large volume of shrimp processing waste available this has seemed a promising source of astaxanthin. However the concentrations are low and the extraction methods attempted have proved expensive.

U.S. Pat. No. 3,906,112 describes the fine grinding of shrimp waste and the mixing and heating of the resulting powder with an oil in order to extract some of the astaxanthin into the oil.

U.S. Pat. No. 4,505,936 describes a similar process but where the chitinous shell is removed and the proteinaceous tissue is acidified before heating with oil.

More recent efforts have used supercritical $CO_2$ to perform the extraction, and U.S. Pat. No. 5,210,186 describes the use of boiling lye to form an alkaline extract.

The common disadvantage to all these methods is that, given the low concentration of astaxanthin present and the high cost of extraction, the astaxanthin extracted is not cost-effective relative to the synthetic alternatives.

Culturing and extracting products via the fermentation of bacteria is well known in industry, and thus considerable effort has been extended in the direction of strain development to this end. U.S. Pat. No. 5,607,839 describes a bacterium belonging to a newly discovered genus that can produce carotenoids including astaxanthin. Similar strain development efforts have also been performed for microalgal sources. Nevertheless, both these sources are still far from commercialization due to the low yields obtained.

Much commercial effort has been expended in recent years on the strain development of the astaxanthin-producing yeast, *P. rhodozyma*. This work has succeeded in producing high yields of astaxanthin by superior strains of *P. rhodozyma*. For example, U.S. Pat. No. 5,599,711 describes a strain of this yeast capable of producing astaxanthin in the thousands of ppm range. However, despite the high yields achieved, this yeast has not proved cost-effective due to the following reasons:

1. When *P. rhodozyma* is added directly to the feed, the bioavailability is low due to its hard cell-wall which hampers the extraction of the astaxanthin molecule by the digestive system of the fish within the digestive time cycle. Attempts to mill or otherwise rupture the cell wall to enhance this bioavailability have only marginally improved the results.
2. The tight binding of the astaxanthin within the cell is the reason behind the relatively expensive nature of the methods for chemically extracting this material from the *P. rhodozyma*. For example, U.S. Pat. No. 5,356,810 discloses the extraction of astaxanthin from dried, unruptured *P. rhodozyma* cells using glacial acetic acid.

There is also extensive literature concerning the extraction of carotenoids in general.

U.S. Pat. No. 5,830,738 describes the use of enzymes to decompose cellular walls so as to extract carotenoids trapped in plant cells.

U.S. Pat. No. 5,789,647 described the use of compressed gases such as butane and propane together with organic entraining agents in order to extract carotenoids from natural materials.

U.S. Pat. No. 5,773,075 describes the use of high-temperature and pressure to extract carotenoids from plant material. However, all these methods are expensive and are thus unsuitable for extracting carotenoids from biomasses in a commercial application.

In accordance with the invention described below, a carotenoid is extracted from a carotenoid source using a mixture of water, a water immiscible solvent and a water soluble co-solvent.

U.S. Pat. No. 4,439,629 discloses extracting β-carotene from algae by treating the algae at 50 to 100° C. with calcium hydroxide to saponify the chlorophyll present and then extracting the β-carotene with a solvent such as methylene chloride, hexane or high boiling petroleum ether.

U.S. Pat. No. 4,871,551 describes extracting astaxanthin from Haematococcus algae by extraction with solvents such as oils, aromatics (e.g. benzene), halogenated hydrocarbons (e.g. methylene chloride), or alkanes (e.g. hexane).

EP-A-612725 describes extraction of β-carotene from halophilic algae of the genus *Dunaliella* including *D. salina, D. parva, D. tertiolecta, D, primolecta* and *D. peircei*. An aqueous suspension of the biomass is emulsified with edible oil (soya bean oil, peanut oil, or sunflower seed oil) at elevated temperatures and the mixture is subjected to membrane ultra-filtration.

WO 98/03480 describes the extraction of β-carotene from algae (*Dunaliella*), vegetables (carrots), or fungi (Blakeslea) by extraction with a water immiscible solvent such as ethyl acetate, butyl acetate, hexane, or vegetable oil, followed by crystallisation and washing of the crystals with a poor solvent for β-carotene, such as ethanol or ethyl acetate.

WO 98/50574 describes extraction of a carotene present as crystals in a biomass by disrupting the cells of the wet biomass, possibly by using a solvent such as octanol, optionally adding a water immiscible solvent which may be oil, hexane or ethyl acetate, and removing debris, to leave solid carotene floating over liquid. The solid upper layer may be washed with water and then with a poor solvent for the carotenoid, such as methanol, ethanol, isopropanol or acetone to remove lipid.

Extraction of β-carotene from natural sources using as solvent one of acetone, methyl-ethyl ketone, methanol, ethanol, propan-2-ol, hexane, dichloromethane and supercritical carbon dioxide is described in U.S. Pat. No. 5,714,658, as is the use of a mixture of an acetic acid ester, such as ethyl acetate, and an edible oil. This however is a combination of two water immiscible solvents.

An extraction protocol for use in an assay for the content of astaxanthin in fish feed is described in "Analytical Methods for Vitamins and Carotenoids in Feed" Ed: P. Hofmann, H. E. Keller, J. Schierle and W. Schüep, Dept. of Vitamin Research and Development—Roche Basel. This involves extraction with a single phase medium of dichloromethane and ethanol.

In summary, although a high-yield natural source for astaxanthin (optimal strains of *P. rhodozyma*) has been developed, it is not currently cost-effective as a salmonid feed additive as the prior art in extraction has not enabled this astaxanthin to be inexpensively extracted and formulated. Similarly, efforts to extract other carotenoids from natural sources have not yet been implemented in a cost-effective manner relative to the cost of their synthetic analogs.

The present invention now provides a process for the extraction of a carotenoid from a carotenoid source comprising treating the carotenoid source at an elevated temperature with a multi-phase solvent mixture comprising water, a hydrophobic carotenoid solvent and a water soluble co-solvent so as to extract the carotenoid from the carotenoid source into the hydrophobic solvent.

Water may be added or may be present naturally in the carotenoid source. The multiphase mixture will of course generally consist of two phases, one mainly aqueous and the other mainly non-aqueous or oily.

The process is preferably carried out at a temperature of from 50° C. upwards, for instance at a temperature of from 50 to 80° C., more preferably from 60 to 70° C.

The biomass is preferably agitated, e.g. stirred, during the treatment.

The extraction is carried on for a suitable period, but preferably for at least 30 minutes, for instance for from 30 minutes to 3 hours, preferably for about 1 hour.

The hydrophobic solvent is preferably chosen to combine its hydrophobic properties with good solvent abilities for the carotenoid and is suitably an edible oil, methyl acetate, ethyl acetate, butyl acetate, a $C_5$ or above alkane or chloroform.

The water soluble co-solvent is preferably chosen to be water soluble and to have at least some limited ability to dissolve the carotenoid, but such that the partition coefficient of the carotenoid between the solvent and the co-solvent is such that carotenoid dissolved in the co-solvent is transferred to the solvent. Suitably the co-solvent is an alcohol, a ketone, an ether, or a cyclic ether. Preferably, the water soluble co-solvent is methanol, ethanol, n-propanol or isopropanol, or is a monoalkyl ester of ethylene glycol (cellosolve), or is 1,3-dioxane or 1,4-dioxane.

A solution of carotenoid in edible oil may be obtained directly by using the edible oil as the solvent but in some circumstances it is advantageous that the hydrophobic solvent is not an edible oil and that following said extraction, the hydrophobic solvent is mixed with edible oil and is evaporated therefrom. The evaporated hydrophobic solvent is preferably then re-used in a said extraction process.

The carotenoid may be astaxanthin, lycopene or beta-carotene, by way of example.

A major field of applicability of the invention is where the carotenoid source is a biomass, such as a yeast of the genus *Phaffia*, shell fish, shell fish waste, krill, algae, fungi, vegetable, or tomato.

However, the process may be used generally for bringing a carotenoid into solution, especially solution in edible oil, and so said carotenoid source may for instance be a carotenoid synthesis reaction mixture or a solid carotenoid obtained by synthesis or previous extraction from a natural source. The invention therefore includes a process of carotenoid synthesis producing a reaction mixture from which a carotenoid is extracted in a work-up procedure including an extraction process as described herein.

The invention further includes a process for preparing a solution of a carotenoid in an edible oil, comprising mixing a solution of said carotenoid in a volatile, water immiscible solvent with said edible oil and evaporating the water immiscible solvent from said mixture.

The invention further provides a process for producing a feed material comprising carrying out a carotenoid extraction process as previously described, so as to provide a solution of carotenoid in edible oil, and adding said solution to feed ingredients.

Preferred features of the invention will be described below. The following discussion and exemplification mostly refers to the extraction and formulation of astaxanthin, although the general application of this method to other carotenoids will be readily understood by one skilled in the art.

Suitably, an aqueous suspension of biomass is heated together with water and an ethanol co-solvent in contact with a hydrophobic solvent such as an consumable oil in which astaxanthin or other carotenoids is readily dissolved. Without wishing to be limited by theory, the water-ethanol mixture serves to: (a) disassociate the protein-carotenoid bonds holding the carotenoid within the cell and (b) remove the carotenoid through the cell wall of the biomass. As astaxanthin is lipophilic and thus is more soluble in a hydrophobic solvent such as oil than in the aqueous co-solvent, the astaxanthin rapidly moves from the aqueous co-solvent to the oil, where this astaxanthin is accumulated. To optimize the contact between the aqueous co-solvent and the oil, the solution is vigorously stirred, thus creating an emulsion. By then separating out the oil layer from the aqueous suspension layer, the astaxanthin is removed in an oil formulation.

The hydrophobic solvent for the astaxanthin may be either an oil or a volatile compound such as ethyl acetate. If it is desired to increase the concentration of astaxanthin in the eventual oil formulation, a two-step process may be used as follows: (1) Ethyl acetate serves as the hydrophobic solvent in the astaxanthin extraction as above, (2) After separation of the layers the astaxanthin-bearing ethyl acetate is mixed in a further vessel with oil and the ethyl acetate is then evaporated off, transferring the astaxanthin to the oil. By recycling such an alternative hydrophobic solvent several times through the oil, the astaxanthin concentration achieved in said oil may thus be increased significantly, thereby advantageously reducing transportation costs.

The astaxanthin-rich oil produced by the process of the present invention may be directly used as an additive to salmonid fish feed, preferably after the addition of suitable anti-oxidants. Bioavailability testing of said additive showed that, advantageously, this astaxanthin-rich oil has a higher bioavailability than that of a commercially-available synthetic product ("Carophyl Pink", from Hoffman La-Roche) and a much higher bioavailability than that of dried *P. rhodozyma* cells.

The carotene is preferably a xanthophyll carotene, i.e. a carotene containing oxygen containing groups (—OH, —O—, or =O).

This process, and its principle of operation will be better understood by reference to the following specific examples:

EXAMPLE 1

Extraction of Astaxanthin from *P. rhodozyma* into Soya Oil with Varying Amounts of Ethanol Wet biomass of *P. rhodozyma* (5 g, dry weight 1 g) was mixed with ethanol (containing the antioxidant propyl gallate, 0.02%) and soya oil. The extraction was carried out under vigorous stirring for 3 h at 65° C. The biomass was removed by filtration, and the astaxanthin-containing soya oil layer was separated.

| Ethanol (ml) | Soya oil (ml) | Astaxanthin Extracted | | |
|---|---|---|---|---|
| | | mg/ml oil | mg/g DW | Recovery (%) |
| 20 | 10 | 0.212 | 2.12 | 58.0 |
| 10 | 10 | 0.496 | 4.96 | 100.0 |

EXAMPLE 2

Extraction of Astaxanthin from *P. rhodozyma* into Soya Oil with Various Amounts of Soya Oil.

Wet biomass of *P. rhodozyma* (5 g, dry weight 1 g) was mixed with ethanol (10.0 ml containing the antioxidant propyl gallate, 0.02%) and soya oil. The extraction was carried out under vigorous stirring for 3 h at 65° C. The biomass was removed by filtration, and the astaxanthin-containing soya oil layer was separated.

| Soya oil (ml) | Astaxanthin Extracted | | |
|---|---|---|---|
| | mg/ml oil | mg/g DW | Recovery (%) |
| 10.0 | 0.490 | 4.90 | 98.8 |
| 3.0 | 1.239 | 3.72 | 75.0 |
| 1.0 | 0.926 | 0.93 | 18.8 |

EXAMPLE 3

Time Course of Astaxanthin Extraction from *P. rhodozyma* into Soya Oil

Wet biomass of *P. rhodozyma* (5 g, dry weight 1 g) was mixed with ethanol (10.0 ml containing the antioxidant propyl gallate, 0.02%) and soya oil (10 ml). The extraction was carried out under vigorous stirring at 65° C. for various lengths of time in order to determine the time required for optimal extraction. Finally, the biomass was removed by filtration, and the astaxanthin-containing soya oil layer was separated.

| Time (hours) | Astaxanthin Extracted | | |
|---|---|---|---|
| | mg/ml oil | mg/g DW | Recovery (%) |
| 0.5 | 0.416 | 4.16 | 83.9 |
| 1.0 | 0.496 | 4.96 | 100.0 |
| 2.0 | 0.487 | 4.87 | 98.2 |
| 3.0 | 0.459 | 4.59 | 92.5 |

EXAMPLE 4

Extraction of Astaxanthin from *P. rhodozyma* with Different Amounts of Soya Oil Based on the result from Example 3 above that approximately 1 hour is the optimal time for the extraction, the following experiment was performed to determine the proportion of oil required to achieve optimal extraction: Wet biomass of *P. rhodozyma* (5 g, dry weight 1 g) was mixed with ethanol (10.0 ml containing antioxidant propyl gallate, 0.02%) and soya oil (10 ml). The extraction was carried out under vigorous stirring at 65° C. for 1 hour. Finally, the biomass was removed by filtration, and the astaxanthin-containing soya oil layer was separated.

| Soya oil (ml) | Astaxanthin Extracted | | |
|---|---|---|---|
| | mg/ml oil | mg/g DW | Recovery (%) |
| 5.0 | 1.008 | 5.04 | 101.6 |
| 1.0 | 0.428 | 4.28 | 86.3 |

Summarising the results of experiments 1 through 4 above, it is clear that the optimal ratio of *P. rhodozyma* (g DW) to ethanol (ml) to soya oil (ml) is approximately 1:10:5 at this scale.

Concentration and Scale-Up

Various routes to increasing the concentration of the astaxanthin in the soya oil were carried out. When the hydrophobic solvent into which the astaxanthin is extracted (i.e. oil) is replaced by an alternate hydrophobic solvent which: (a) has a high affinity for astaxanthin, and (b) has a low boiling point, then this solvent can be used to transfer the astaxanthin into the oil in a second step, as described in the experiment below:

EXAMPLE 5

Extraction of Astaxanthin into Ethyl Acetate

Wet biomass of *P. rhodozyma* (1.5 kg, dry weight 0.3 kg) was mixed with ethanol (1.2 liters) containing the antioxidant propyl gallate, (0.02%) and ethyl acetate (1.2 liters). The extraction was carried out under vigorous stirring at 60° C. for 1 hour. Finally, the biomass was removed by filtration, and the astaxanthin-containing ethyl acetate layer was separated. The ethyl acetate layer was combined with soya oil (100 ml) and the ethyl acetate was removed by evaporation. This procedure yielded 1.49 g astaxanthin at the concentration of 14.9 mg per ml oil. By repeating this process using the same oil sample, the astaxanthin accumulates in the oil at higher and higher concentrations.

As will be clear to one skilled in the art, various engineering configurations can be used to scale-up the process of the present invention to an industrial level process. In a preferred embodiment, the astaxanthin extraction is performed in the following stages:

i) Wet biomass of P. rhodozyma is taken from a fermentor, separated from the fermentation broth and placed in a first vessel,
ii) the astaxanthin extraction is performed into ethyl acetate in this first vessel as described above (example 5),
iii) the vigorous stirring is halted at which point the aqueous layer (including the biomass) separates out from the ethyl acetate layer,
iv) the ethyl acetate is drained into a second vessel in which an edible oil is present,
v) the aqueous layer is filtered, the ethanol retrieved for re-use and the used biomass is discarded into a waste stream,
vi) the first vessel has a further batch of wet biomass input to it together with the re-cycled ethanol,
vii) the ethyl acetate in the second vessel is then evaporated off via a pipe that terminates in the first vessel and is thus re-cycled to the first vessel,
viii) the astaxanthin-rich edible oil in the second vessel can then either be output from the process at this point, or steps b) through g) can be repeated a number of times before this oil is output.

It is readily apparent that the concentration achieved in the oil produced is a function of the ratio of ethyl acetate to oil in the second vessel and the number of times that steps b) through g) are repeated. Some fraction of the solvents will always be lost and this quantity will be replaced as they are recycled. The presence of anti-oxidants throughout the process serves to minimize the amount of astaxanthin lost during processing due to oxidation.

Generality of Process

The generality of the process of the current invention to a range of biomasses, carotenoids and oils was determined by demonstrating: (a) astaxanthin extraction from a number of different astaxanthin-containing sources into both fish oil and soya oil in examples 6 through 8, and (b) lycopene extraction from tomatoes.

EXAMPLE 6

Extraction of Astaxanthin from Various Sources into Fish Oil

Wet biomass of P. rhodozyma (5 g, dry weight 1 g) was mixed with ethanol (10.0 ml containing antioxidant propyl gallate, 0.02%) and fish oil (5 ml). The extraction was carried out under vigorous stirring at 65° C. for 1 hour. Finally, the biomass was removed by filtration, and the astaxanthin-containing fish oil layer was separated.

Dried krill hydrolysate, frozen krill and shrimp meal (1 g of each) were extracted with ethanol (5 ml, containing propyl gallate, 0.02%) and fish oil (2.0 ml) at 65° C. for 0.5 hours.

| | Astaxanthin Extracted | | |
| --- | --- | --- | --- |
| Material | mg/ml oil | Mg/g DW | Recovery (%) |
| Dried krill hydrolyzate | 0.309 | 0.618 | 100.0 |
| Frozen krill | 0.268 | 0.574 | 100.0 |
| Shrimp meal | 0.029 | 0.059 | 64.1 |
| P. rhodozyma | 0.990 | 4.550 | 91.8 |

EXAMPLE 7

Extraction of Astaxanthin from Various Sources into Soya Oil

Dried krill hydrolyzate (5 g), was extracted with ethanol (20 ml, containing propyl gallate, 0.02%) and soya oil (2.5 ml). Frozen krill and shrimp meal (10 g of each) were extracted with 40 ml of ethanol and 2.5 ml oil. The extraction was carried out under vigorous stirring at 65° C. for 1 hour. The biomass was removed by filtration, and the astaxanthin-containing soya oil layers were separated.

| | Astaxanthin Extracted | | |
| --- | --- | --- | --- |
| Material | mg/ml oil | Mg/g DW | Recovery (%) |
| Dried krill hydrolyzate | 0.445 | 0.470 | 36 |
| Frozen krill | 0.249 | 0.265 | 46 |
| Shrimp meal | 0.113 | 0.028 | 30 |

EXAMPLE 8

Extraction of Astaxanthin from Various Sources with Addition of Water

The astaxanthin source was mixed with various quantities of water and ethanol containing the antioxidant propyl gallate (0.02%), and soya oil (2.5 ml). The extraction was carried out under vigorous stirring at 65° C. for 1 hour. Finally, the biomass was removed by filtration, and the astaxanthin-containing fish oil layer was separated. Group C (tanks 9–11) were fed the additive according produced using the process of the present invention.

The table below gives the results of bioavailability tests:

| Test Group | Bioavailability (relative to Group A as a reference, based on analysed pigment concentration in the fillet) |
| --- | --- |
| Group A | 100% |
| Group B | 15% |
| Group C | 110% |

According to these results, the formulation prepared according to the process of the present invention had increased bioavailability relative to both the existing synthetic products and to the direct consumption of the P. rhodozyma.

An additional advantage of this formulation is that oil is in any case a major component of salmonid feed and so the formulation is readily incorporated in existing feed-production processes. A yet further advantage of this formulation is that, being a liquid, it is simple to add the appropriate liquid anti-oxidants in order to stabilize it against oxidation.

The exemplified process provides an improved and cost-effective process for the efficient extraction of carotenoids from biomasses. A further advantage of the process vis-à-vis the direct addition of P. rhodozyma to fish feed is that in the latter case the P. rhodozyma needs to be dried before transportation. As the process of the present invention uses wet P. rhodozyma, the costs involved in drying the P. rhodozyma may be saved, although the process can of course be applied to P. rhodozyma that has been partially dried or has been dried and is then made wet again for the extraction process.

A further advantage is an increase in the process stability of the carotenoids during the process of adding them to other feed components to make an animal feed.

It will be readily understood by one skilled in the art that numerous engineering modifications of the process of the current invention may be implemented, including using a two or multi-chamber apparatus and recycling the solvents and/or extractants. Similarly, by the use of various ratios of biomass, aqueous co-solvent and hydrophobic solvent, astaxanthin can be extracted from several cellular biomasses and other carotenoids can be extracted from their respective natural sources.

What is claimed is:

1. A process for the extraction of a carotenoid from a biomass carotenoid source comprising treating the biomass at an elevated temperature with a solvent mixture comprising water, a hydrophobic carotenoid solvent and a water miscible co-solvent so as to form an aqueous phase and a non-aqueous phase containing the hydrophobic solvent and to extract the carotenoid from the biomass into the hydrophobic solvent wherein the process is carried out at a temperature of from 50° C. upwards.

2. A process as claimed in claim 1, wherein the process is carried out at a temperature of from 50 to 80° C.

3. A process as claimed in claim 1, wherein the process is carried out at a temperature of from 60 to 70° C.

4. A process as claimed in claim 1, wherein the biomass source and solvent mixture are agitated during the treatment.

5. A process as claimed in claim 1, wherein the extraction is carried on for at least 30 minutes.

6. A process as claimed in claim 5, wherein the extraction is carried on for from 30 minutes to 3 hours.

7. A process as claimed in claim 6, wherein the extraction is carried on for about 1 hour.

8. A process as claimed in claim 1, wherein the hydrophobic solvent is an edible oil, methyl acetate, ethyl acetate, butyl acetate, a $C_5$ or above alkane or chloroform.

9. A process as claimed in claim 1, wherein the water miscible co-solvent is an alcohol, a ketone, an ether, or a cyclic ether.

10. A process as claimed in claim 9, wherein the water miscible co-solvent is methanol, ethanol, n-propanol or iso-propanol, or is a monoalkyl ester of ethylene glycol (cellosolve) or is 1,3-dioxane or 1,4-dioxane.

11. A process as claimed in claim 1, wherein the hydrophobic solvent is not an edible oil and wherein following said extraction, the hydrophobic solvent is mixed with edible oil and is evaporated therefrom.

12. A process as claimed in claim 11, wherein the evaporated hydrophobic solvent is re-used in a said extraction process.

13. A process as claimed in claim 1, wherein the carotenoid is astaxanthin, lycopene or beta-carotene.

14. A process as claimed in claim 1, wherein the biomass is a yeast of the genus Phaffia, shell fish, shell fish waste, krill, algae, fungi, vegetable, or tomato.

15. A process for producing a feed material comprising carrying out a carotenoid extraction process as claimed in claim 1, so as to provide a solution of carotenoid in edible oil, and adding said solution to feed ingredients.

16. A process for preparing a solution of a carotenoid in an edible oil, comprising mixing a solution of said carotenoid in a volatile, water immiscible solvent with said edible oil and evaporating the water immiscible solvent from said mixture.

* * * * *